(12) United States Patent  (10) Patent No.: US 8,820,322 B1
Gordon  (45) Date of Patent: Sep. 2, 2014

(54) WATER FILLED UNITARY FLEXIBLE POUCH FOR USE WITH HEATING ELEMENT

(76) Inventor: Sloan Gordon, Houston, TX (US)

( * ) Notice: Subject to any disclaimer, the term of this patent is extended or adjusted under 35 U.S.C. 154(b) by 913 days.

(21) Appl. No.: 12/409,907

(22) Filed: Mar. 24, 2009

Related U.S. Application Data

(60) Provisional application No. 61/059,157, filed on Jun. 5, 2008.

(51) Int. Cl.
*A61M 16/10* (2006.01)

(52) U.S. Cl.
USPC .................................................. 128/203.16

(58) Field of Classification Search
USPC .......... 606/28; 604/122; 128/203.16, 203.17; 261/72.1, 119.1, 142, DIG. 65; 122/DIG. 10, DIG. 11; 383/41, 105
See application file for complete search history.

(56) References Cited

U.S. PATENT DOCUMENTS

| | | | |
|---|---|---|---|
| 3,211,144 A * | 10/1965 | Nehring | 604/409 |
| 3,304,977 A * | 2/1967 | Hammons | 604/409 |
| 3,871,373 A * | 3/1975 | Jackson | 128/203.27 |
| 4,012,473 A * | 3/1977 | Lindsey et al. | 261/142 |
| 4,131,200 A * | 12/1978 | Rinfret | 206/484 |
| 4,152,379 A * | 5/1979 | Suhr | 261/142 |
| 4,624,806 A | 11/1986 | Koszyk | |
| 4,943,704 A | 7/1990 | Rabenau et al. | |
| 5,231,979 A * | 8/1993 | Rose et al. | 128/204.14 |
| 5,520,004 A * | 5/1996 | Jones, III | 62/63 |
| 5,769,232 A * | 6/1998 | Cash et al. | 206/522 |
| 6,398,197 B1 * | 6/2002 | Dickinson et al. | 261/141 |
| 6,854,888 B1 * | 2/2005 | Brown et al. | 383/80 |
| 8,029,885 B2 * | 10/2011 | Manabe et al. | 428/215 |
| 2001/0030021 A1 * | 10/2001 | Romig et al. | 156/308.2 |
| 2004/0022676 A1 * | 2/2004 | Hamilton et al. | 422/37 |
| 2008/0255267 A1 * | 10/2008 | Domb et al. | 523/124 |
| 2009/0000620 A1 * | 1/2009 | Virr | 128/203.27 |
| 2011/0064901 A1 * | 3/2011 | Blackburn et al. | 428/43 |

\* cited by examiner

*Primary Examiner* — Lynne Anderson
*Assistant Examiner* — Bradley Philips
(74) *Attorney, Agent, or Firm* — Buskop Law Group, PC; Wendy Buskop

(57) ABSTRACT

A water filled unitary flexible pouch for use with a heating element for delivering humidified air to a user, comprising a disposable pouch formed from a first and a second flexible polymer sheet sealed to the first flexible polymer sheet, wherein the second flexible polymer sheet comprises a flexible metalized area adapted to contact the heating element. A premeasured amount of distilled water is in the disposable pouch in contact with the flexible metalized area, and forms vaporized water when the flexible metalized area contacts the heating element. An integral inlet port is used to flow continuous pressurized air into the disposable pouch at a titrated pressure ranging from about 4 centimeters of water to about 30 centimeters of water, and an integral outlet port is used to flow vaporized water and pressurized air from the disposable pouch at a pressure up to about 30 centimeters of water.

16 Claims, 2 Drawing Sheets

WATER FILLED UNITARY FLEXIBLE POUCH FOR USE WITH HEATING ELEMENT

CROSS REFERENCE TO RELATED APPLICATIONS

The present application claims priority to co-pending U.S. Provisional Application Ser. No. 61/059,157 filed on Jun. 5, 2008, entitled "Water Filled Unitary Flexible Pouch for Use with Heating Element" and is incorporated in its entirety herein.

FIELD

The present embodiments generally relate to a water filled unitary flexible pouch for use with a heating element for delivering humidified air to a user.

BACKGROUND

A need exists for a water filled unitary flexible pouch, useable with a humidifier, that is lightweight, inexpensive to produce, easy and efficient to use.

A further need exists for a water filled unitary flexible pouch, useable with a humidifier, that contains a premeasured amount of distilled water, and that is disposable after a single use, avoiding the need for cleaning, disassembly, or measuring water for refilling the device.

The present embodiments meet these needs.

BRIEF DESCRIPTION OF THE DRAWINGS

The detailed description will be better understood in conjunction with the accompanying drawings as follows.

Figure 1:
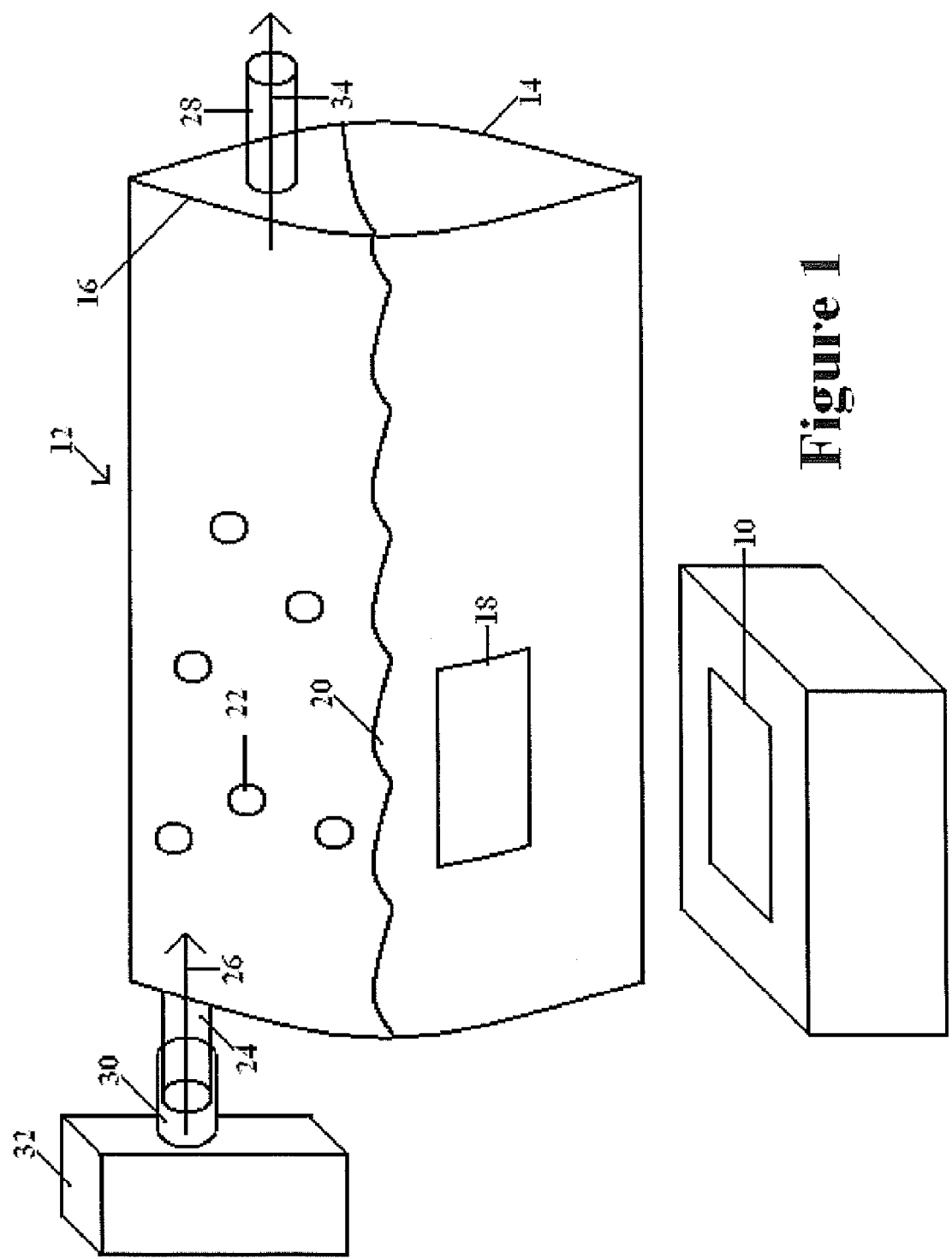
FIG. 1 depicts an embodiment of the present water filled unitary flexible pouch.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments relate to a water filled unitary flexible pouch for use with a heating element for delivering humidified air to a user.

Conventional humidifier tanks are made from plastic or other inflexible materials, and are typically multi-part devices that require assembly and disassembly for storage and use. Once assembled, a conventional humidifier tank must be filled with a specific quantity of distilled water that must be carefully measured. After use, a conventional humidifier tank must be either refilled with a measured quantity of distilled water, or disassembled and cleaned.

The present flexible pouch can be a unitary device, which can be formed from flexible polymer sheets, that advantageously requires no assembly or disassembly. Further, the present flexible pouch can be lightweight and compressible, facilitating easy storage and transport.

The present flexible pouch can contain a premeasured amount of distilled water, and therefore requires no separate purchase and provision of distilled water, and no meticulous measurement of water, saving time, tedium, and money.

Additionally, the present flexible pouch can be inexpensive to produce and use, and is advantageously disposable after a single use, if desired. Thus, the present flexible pouch does not require cleaning, refilling, or maintenance.

The present flexible pouch can be useable to provide humidified air for a wide variety of applications, including but not limited to the delivery of pressurized air to a C-Pap machine for treating patients diagnosed with sleep apnea. Typically, a C-Pap machine provides air at a titrated pressure, measured in centimeters of water, which is determined by a sleep physician following an overnight study of a patient. Most sleep apnea patients are treated with a titrated pressure ranging from 6 centimeters to 14 centimeters of water, a typical C-Pap machine is able to deliver pressures ranging from 4 centimeters to 20 centimeters of water. Specialized C-Pap machines can deliver pressures up to 25 centimeters or 30 centimeters of water.

The refilling of a humidifier attached to a C-Pap machine is tedious and cumbersome, especially for elderly individuals and individuals with physical disabilities. Distilled water is typically purchased in heavy, bulky gallon containers from a drug store or supermarket, causing pouring and proper measurement of the distilled water to be difficult.

The present single-use flexible pouch can be easy to use, always contains the correct, premeasured quantity of distilled water, and can be generally transparent, so that a user can see when the pouch is empty.

A large issue with C-Pap machines and the treatment of sleep apnea is patient compliance. The difficulties inherent in purchasing distilled water, measuring the distilled water and filling a conventional humidifier tank, especially when an individual is preparing for bed, often lead to a lack of patient compliance.

The present flexible pouch can be purchased in bulk, and each pouch can be ready-to-use immediately. The flexible pouches can be placed into a humidification device to replace the conventional plastic chamber that normally comes with a C-Pap machine, eliminating a great deal of the difficulty and tedium inherent in the use of the C-Pap machine.

The present pouch thereby can facilitate treatment of sleep apnea, and patient compliance with sleep apnea treatment programs. The present flexible pouch can prevent accidents and injuries caused by fatigue related to sleep apnea and increase productivity of users.

The present flexible pouch also can provide the benefit of improved safety and a decreased risk of electrical shock and/or equipment damage compared to conventional humidifier tanks. When filling a humidifier tank using a gallon of distilled water, many users, especially those having diminished physical capability or eyesight, may spill water on the electrical circuits that link the C-Pap machine to a humidifier, which has a heating element plugged into an electrical outlet. Use of the present flexible pouch, which can be purchased already containing a premeasured quantity of distilled water, can prevent the electrical hazards associated with spilled water, thereby avoiding electrical shock and damaged equipment.

The embodiments can be contemplated to be usable with any type of heating element, such as a built-in humidifier present in a HC Thermosmart or Sleepstyle Thermosmart C-Pap machine, made by Fisher & Paykel of Queensland, Australia.

A disposable pouch can be formed from a first flexible polymer sheet and a second flexible polymer sheet sealed to the first flexible polymer sheet. The polymer sheets can include transparent polymers, including polyolefin polymers, polypropylene, polybutylene, polyvinyl chloride, polyethylene, other homopolymers and copolymers, or combinations thereof.

In an embodiment, the disposable pouch can be formed from a multilayer structure. For example, one or both of the flexible polymer sheets can have a first layer formed from a first material, such as polyethylene, and a second layer formed from a differing material, such as polyolefin.

The flexible polymer sheets can have a thickness ranging from about 0.5 millimeters to about 5 millimeters, or more.

In another embodiment, the disposable pouch can be at least partially formed from a biodegradable material, such as oil-based biodegradable plastics, starch-based biodegradable plastics, polyhydroxyalkanoate, polylactic acid, poly-3-hydroxybutyrate, polyamide 11, or other similar partially or wholly biodegradable materials. The embodiments can be contemplated to minimize any negative environmental impacts created through the disposal of the present water filled unitary flexible pouch.

The disposable pouch, while compressible, is contemplated to have a length ranging from about 1 inch to about 12 inches, a width ranging from about 1 inch to about 12 inches, and a depth ranging from about 0.25 inches to about 6 inches. The maximum volume of the disposable pouch can range from about 50 milliliters to about 500 milliliters, or more. The disposable pouch can be rectangular, square, round, elliptical, or have other shapes.

The second flexible polymer sheet can include a flexible metalized area adapted to contact a heating element. The flexible metalized area can include any flexible metallic conductor, including aluminum foil, steel foil, or combinations thereof. In an embodiment, the flexible metalized area can have a thickness ranging from about 1 millimeter to about 5 millimeters.

The flexible metalized area can range from about 5 percent to about 95 percent of the area of the second flexible polymer sheet, and can have any shape. For example, the flexible metalized area can be a rectangular area having a length of about 2 inches and a width of about 1 inch, disposed within a flexible polymer sheet having a length of about 8 inches and a width of about 4 inches.

The disposable pouch can contain a premeasured amount of distilled water, in contact with the flexible metalized area, such that the distilled water can be vaporized when the flexible metalized area contacts the heating element.

In an embodiment, the premeasured amount of distilled water can range from about 50 milliliters to about 200 milliliters.

The premeasured amount of distilled water can include one or more additional ingredients, such as saline, fragrances, moisturizers, medications or combinations thereof, which can include menthol, eucalyptus, aloe, emu oil, white oil, and/or other similar petroleum emollients.

In an embodiment, the amount of moisturizer, saline, fragrance, medication or combinations thereof, can range from about 0.1 percent to about 2.0 percent by weight based on the total amount of distilled water.

In another contemplated embodiment, the amount of saline can include from about 0.8 percent to about 1.0 percent by weight sodium chloride, such as a solution of distilled water containing about 0.9 percent sodium chloride by weight.

An integral inlet port can be in communication with the disposable pouch for flowing continuous pressurized air into the disposable pouch at a pressure ranging from about 4 centimeters of water to about 30 centimeters of water. The integral inlet port can be made from rubber, plastic, the same or differing polymers from the disposable pouch, or other similar materials.

In an embodiment, the integral inlet port can have a length ranging from about 0.5 inches to about 12 inches, an inner diameter ranging from about 0.1 inches to about 1 inch, and an outer diameter ranging from about 0.25 inches to about 2 inches.

An integral outlet port can also be in communication with the disposable pouch for flowing vaporized water and pressurized air out of the disposable pouch at a pressure up to about 30 centimeters of water.

The integral outlet port can be made from similar materials as the integral inlet port, and can have dimensions similar to those of the integral inlet port.

In an embodiment, the integral inlet port can be in communication with a hose, such as a flexible rubber, plastic, or polymer hose with a length ranging from about 1 inch to about 3 feet, or more, an inner diameter ranging from about 0.1 inch to about 2 inches, and an outer diameter ranging from about 0.25 inches to about 3 inches. The hose can be connected to a C-Pap machine, such as those produced by Fisher & Paykel of Queensland, Australia.

In an embodiment, the flexible pouch can be integral with a C-Pap machine, in lieu of connection via a hose or similar means. For example, the present flexible pouch can be placed internally in a C-Pap machine, in place of a typical water tank. An internal heating element of the C-Pap machine can be used to heat the distilled water, which can mix with the ambient pressurized air provided by the C-Pap machine.

Referring now to FIG. 1, an embodiment of the water filled unitary flexible pouch is depicted.

FIG. 1 depicts a disposable pouch (12) formed from a first flexible polymer sheet (14), which is depicted as a rectangle having a length of about 8 inches and a width of about 6 inches, which can be sealed to a second flexible polymer sheet (16) of approximately the same size and shape. It is contemplated that the depicted flexible polymer sheets (14, 16) can be transparent and can be made from polyolefin, polyethylene, or combinations thereof. The depicted flexible polymer sheets (14, 16) can be contemplated to range from about 1 millimeter to about 5 millimeters in thickness.

The depicted disposable pouch (12) can have a maximum volume of about 240 milliliters to about 250 milliliters, and is shown containing a premeasured amount of distilled water (20) that can fill the disposable pouch (12) approximately halfway. The premeasured amount of distilled water (20) can be contemplated to be about 120 milliliters.

The second flexible polymer sheet (16) is shown including a flexible metalized area (18), which is depicted as a rectangular section, which can be made of aluminum or steel foil disposed within the second flexible polymer sheet (16), having a length of about 2 inches, a width of about 1 inch, and a thickness ranging from about 1 millimeter to about 5 millimeters.

It can be contemplated that when the flexible metalized area (18) is placed in contact with a heating element (10), heat from the heating element (10) is conducted through the flexible metalized area (18) to heat the premeasured amount of distilled water (20), forming vaporized water (22). The heat from the heating element (10) can be contemplated to be sufficient to raise the temperature of the premeasured amount of distilled water (20) to about 100 degrees Centigrade, without exceeding the heat tolerance of the disposable pouch (12).

An integral inlet port (24) is shown in communication with the disposable pouch (12). The integral inlet port (24) is depicted as a flexible tube, which can be made of plastic having a length of about 1 inch and a diameter of about 0.5 inches.

The integral inlet port (24) is shown in communication with a C-Pap machine (32) via a hose (30), which is depicted as a short, flexible hose, which can be made of rubber or plastic, with a diameter slightly greater than that of the integral inlet port (24). Any type of clamp, fastener, adhesive, or other engagement can be used to secure the hose (30) to the integral inlet port (24). The hose (30) can also form a secure engagement with the integral inlet port (24) independent of any fastener, clamp, or adhesive.

An integral outlet port (28), is also shown in communication with the disposable pouch (12). The integral outlet port (28) is depicted as a flexible tube, which can be made of plastic, having a length of about 1 inch and a diameter of about 0.5 inches.

FIG. 1 depicts pressurized air (26) flowed by the C-Pap machine (32), at a titrated pressure ranging from about 4 centimeters of water to about 30 centimeters of water, through the hose (30) and integral inlet port (24) into the disposable pouch (12). Within the disposable pouch (12), the pressurized air (26) can mix with the vaporized water (22), to form humidified air (34).

FIG. 1 depicts the humidified air (34) flowing out of the disposable pouch (12) through the integral outlet port (28).

The depicted disposable pouch (12) can thereby function as a flexible, single-use humidifier, containing a premeasured quantity of distilled water (20), for formation of humidified air (34).

Figure 2:
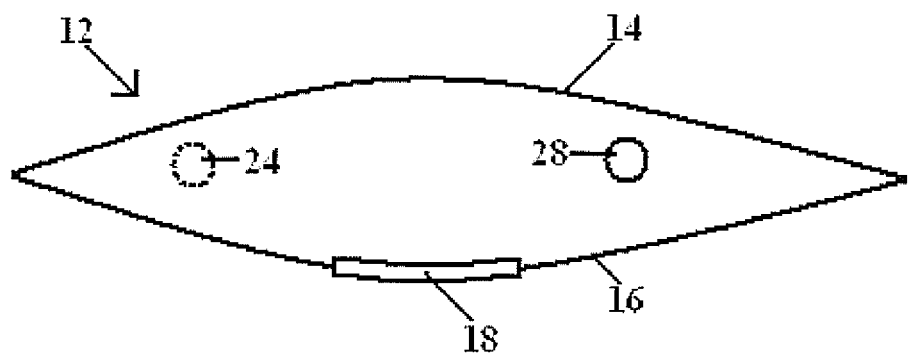
FIG. 2 depicts a side cross-sectional view of the water filled unitary flexible pouch of FIG. 1.

Referring now to FIG. 2, a side cross-sectional view of the water filled unitary flexible pouch of FIG. 1 as shown.

FIG. 2 depicts the disposable pouch (12), formed from the first flexible polymer sheet (14) sealed to the second flexible polymer sheet (16). The second flexible polymer sheet (16) can have a flexible metalized area (18).

FIG. 2 depicts the flexible metalized area (18) having a thickness slightly greater than that of the flexible polymer sheets (14, 16). It can be contemplated that the thickness of the flexible metalized area (18) can range from about 1 millimeter to about 5 millimeters, while the thickness of the flexible polymer sheets (14, 16) can range from about 0.5 millimeters to about 5 millimeters.

The integral inlet port (24) and integral outlet port (28) are shown in communication with the disposable pouch (12).

Figure 3:
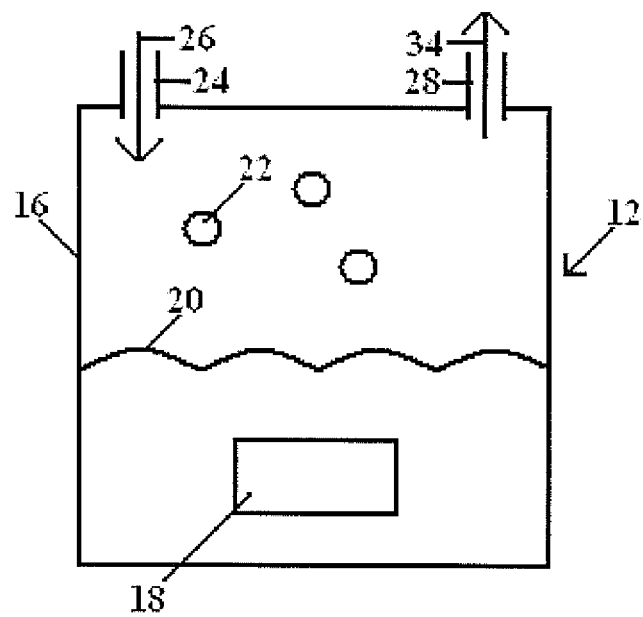
FIG. 3 depicts a front view of an alternate embodiment of the present water filled unitary flexible pouch.

Referring now to FIG. 3, a front view of an embodiment of the water filled unitary flexible pouch is depicted. The depicted embodiment can be contemplated to have the general shape and appearance of a plastic intravenous drip bag or pouch.

A disposable pouch (12) is shown having a second flexible polymer sheet (16), which can be sealed to a first flexible polymer sheet (not visible in FIG. 3). A premeasured quantity of distilled water (20) can be contained within the disposable pouch (12).

The second flexible polymer sheet (16) can have a flexible metalized area (18), which can vaporize the premeasured quantity of distilled water (20) when placed in contact with a heating element (also not shown in FIG. 3), forming vaporized water (22).

FIG. 3 depicts an integral inlet port (24) and an integral outlet port (28), which can be disposed near the top of the disposable pouch (12). Pressurized air (26) is shown flowing into the disposable pouch (12) through the integral inlet port (24). The pressurized air (26) can be contemplated to mix with the vaporized water (22) to form humidified air (34), which is shown flowing from the disposable pouch (12) through the integral outlet port (28).

While these embodiments have been described with emphasis on the embodiments, it should be understood that within the scope of the appended claims, the embodiments might be practiced other than as specifically described herein.

What is claimed is:

1. A water filled unitary flexible pouch for use with a heating element for delivering humidified air to a user, wherein the water filled unitary flexible pouch comprises:
   a. a disposable pouch comprising:
      (i) a first flexible polymer sheet; and
      (ii) a second flexible polymer sheet sealed to the first flexible polymer sheet, forming a closed chamber therebetween, wherein the closed chamber has a first end and a second end, wherein the second flexible polymer sheet comprises a flexible metalized area adapted to contact the heating element and conducting heat to the water within;
   b. a premeasured amount of distilled water contained within the closed chamber of the disposable pouch in contact with the flexible metalized area, wherein the premeasured amount of distilled water forms vaporized water when the flexible metalized area contacts the heating element;
   c. an integral inlet port disposed through the first end for flowing continuous pressurized air at a titrated pressure into the disposable pouch; and
   d. an integral outlet port disposed through the second end for flowing vaporized water and pressurized air from the disposable pouch, wherein the integral outlet port is disposed through the disposable pouch and above the premeasured amount of distilled water contained within the disposable pouch; and
      wherein the disposable pouch is integral with a C-Pap machine.

2. The water filled unitary flexible pouch of claim 1, wherein the first flexible polymer sheet and the second flexible polymer sheet comprise a transparent polymer.

3. The water filled unitary flexible pouch of claim 2, wherein the transparent polymer comprises a polyolefin polymer, a homopolymer, a copolymer, or combinations thereof.

4. The water filled unitary flexible pouch of claim 1, wherein the disposable pouch is formed from a multilayer structure.

5. The water filled unitary flexible pouch of claim 4, wherein the multilayer structure has at least a first layer comprising a first material, and at least a second layer comprising a second material that is different from the first material.

6. The water filled unitary flexible pouch of claim 1, wherein the flexible metalized area comprises aluminum foil, steel foil, or combinations thereof, having a thickness ranging from 1 millimeter to 5 millimeters.

7. The water filled unitary flexible pouch of claim 1, wherein the flexible metalized area comprises from 5 percent to 95 percent of the second flexible polymer sheet.

8. The water filled unitary flexible pouch of claim 1, wherein the premeasured amount of distilled water further comprises at least one member of the group consisting of: saline, fragrances, moisturizers, medications and combinations thereof.

9. The water filled unitary flexible pouch of claim 8, wherein the saline comprises from 0.8 percent by weight to 1.0 percent by weight sodium chloride.

10. The water filled unitary flexible pouch of claim 8, wherein the amount of moisturizers, saline, fragrances, medications or combinations thereof, ranges from 0.1 percent by weight to 2.0 percent by weight based on the total amount of the premeasured amount of distilled water.

11. The water filled unitary flexible pouch of claim 1, wherein the premeasured amount of distilled water ranges from 50 milliliters to 200 milliliters.

12. The water filled unitary flexible pouch of claim 1, wherein the integral inlet port communicates with a hose connected to the C-Pap machine.

13. The water filled unitary flexible pouch of claim 1, wherein the disposable pouch is at least partially formed from an at least partially biodegradable material.

14. The water filled unitary flexible pouch of claim 1, wherein the integral inlet port is disposed through the disposable pouch and above the premeasured amount of distilled water contained within the disposable pouch.

15. The water filled unitary flexible pouch of claim 14, wherein the disposable pouch comprises a first portion having the premeasured amount of distilled water disposed therein and a second portion having the vaporized water and the pressurized air disposed therein, and wherein the integral inlet port and the integral outlet port are both in fluid communication with the second portion.

16. The water filled unitary flexible pouch of claim 1, wherein the titrated pressure ranges from 4 centimeters of water to 30 centimeters of water, and wherein the pressurized air is at a pressure of up to 30 centimeters of water.

* * * * *